United States Patent
Haynes (10) Patent No.: US 8,776,299 B2
(45) Date of Patent: *Jul. 15, 2014

(54) TOOTHBRUSH HEAD

(75) Inventor: Ronald W. Haynes, Fairfield Bay, AZ (US)

(73) Assignee: Den-Mat Holdings, LLC, Lompoe, CA (US)

( * ) Notice: Subject to any disclaimer, the term of this patent is extended or adjusted under 35 U.S.C. 154(b) by 157 days.

This patent is subject to a terminal disclaimer.

(21) Appl. No.: 13/493,928

(22) Filed: Jun. 11, 2012

(65) Prior Publication Data

US 2013/0145567 A1  Jun. 13, 2013

Related U.S. Application Data

(62) Division of application No. 13/274,222, filed on Oct. 14, 2011, now Pat. No. 8,196,246.

(51) Int. Cl.
*A46B 13/02* (2006.01)

(52) U.S. Cl.
USPC .................................................. 15/22.1; 15/28

(58) Field of Classification Search
USPC .......... 15/22.1, 22.2, 22.4, 167.1, 23, 28, 179
See application file for complete search history.

(56) References Cited

U.S. PATENT DOCUMENTS

| | | | |
|---|---|---|---|
| 3,802,420 A | 4/1974 | Moffat | |
| 4,315,741 A | 2/1982 | Reichl | |
| D278,764 S | 5/1985 | Olsen | |
| 5,311,632 A | 5/1994 | Center | |
| 5,544,382 A | 8/1996 | Giuliani et al. | |
| D411,769 S | 7/1999 | Wright | |
| 5,930,858 A | 8/1999 | Jung | |
| D423,224 S | 4/2000 | Sale et al. | |
| D436,254 S | 1/2001 | King et al. | |
| D480,875 S | 10/2003 | De Salvo | |
| D483,183 S | 12/2003 | De Salvo | |
| D487,636 S | 3/2004 | De Salvo | |
| D489,183 S | 5/2004 | Akahori et al. | |
| 6,779,215 B2 | 8/2004 | Hartman et al. | |
| D503,852 S | 4/2005 | Hensel | |
| D534,727 S | 1/2007 | Vu | |
| D534,728 S | 1/2007 | Vu | |
| D577,199 S | 9/2008 | Zhuan | |
| 8,196,246 B1 * | 6/2012 | Haynes | 15/22.1 |
| 2004/0025272 A1 | 2/2004 | Stvartak et al. | |
| 2006/0137117 A1 * | 6/2006 | Chan | 15/22.1 |
| 2007/0006402 A1 | 1/2007 | Kang | |
| 2008/0196184 A1 | 8/2008 | Mary T. | |
| 2008/0313829 A1 | 12/2008 | Dabrowski | |
| 2010/0269276 A1 | 10/2010 | Faranda et al. | |
| 2011/0056033 A1 | 3/2011 | Iwahori et al. | |

OTHER PUBLICATIONS

Images of Rota-dent toothbrush head and assembly. This product was on sale more than one year before the filing of U.S. Appl. No. 29/404,462.

* cited by examiner

*Primary Examiner* — Robert Scruggs
(74) *Attorney, Agent, or Firm* — Frederick W. Tong (57) ABSTRACT

A toothbrush head that includes a main body portion and a generally cylindrical connection member extending downwardly and defining an axis. The connection member includes bottom, outer and inner surfaces and a central opening. The connection member also includes a first lower protrusion that includes first and second inclined surfaces extending inwardly from the inner surface, a first slot defined in the bottom surface and the inner surface, a first lower notch defined in the inner surface, and a first opening defined in the inner surface above the first lower protrusion.

7 Claims, 7 Drawing Sheets

TOOTHBRUSH HEAD

CROSS REFERENCE TO RELATED APPLICATIONS

This application is a divisional of U.S. patent application Ser. No. 13/274,222, filed Oct. 14, 2011, the entirety of which is incorporated herein by reference

FIELD OF THE INVENTION

The present invention relates to a connection system, and more particularly to a system for connecting an electric toothbrush handle and head.

BACKGROUND OF THE INVENTION

After a certain amount of use, the brush heads on electric toothbrushes often wear out and need to be replaced. A connection system for connecting a new head to the handle that is easy for a consumer to use is desirable.

SUMMARY OF THE PREFERRED EMBODIMENTS

In accordance with a first aspect of the present invention there is provided a toothbrush head that includes a main body portion and a generally cylindrical connection member extending downwardly from the main body portion. The connection member defines an axis and includes a bottom surface, an outer surface and an inner surface that defines a central opening, a first lower protrusion includes first and second inclined surfaces extending inwardly from the inner surface, a first slot defined in the bottom surface and the inner surface, a first lower notch defined in the inner surface, and a first opening defined in the inner surface above the first lower protrusion. The first slot and the first lower notch are disposed on opposite sides of the first lower protrusion.

In accordance with another aspect of the present invention, there is provided a toothbrush that includes a handle and head. The handle includes a main body portion and a neck extending upwardly from the main body portion. The neck includes first upper and lower tabs and a first lug positioned between the first upper and lower tabs. The neck also includes second upper and lower tabs and a second lug positioned between the second upper and lower tabs. The head includes a main body portion and a generally cylindrical connection member extending downwardly and defining an axis. The connection member includes bottom, outer and inner surfaces and a central opening. The connection member also includes a first lower protrusion that includes first and second inclined surfaces extending inwardly from the inner surface, a first slot defined in the bottom surface and the inner surface, a first lower notch defined in the inner surface, and a first opening defined in the inner surface above the first lower protrusion. The first slot and the first lower notch are disposed on opposite sides of the first lower protrusion, the first lower tab is positioned in the first lower notch and the first lug is positioned in the first opening.

In accordance with another aspect of the present invention, there is provided a method of connecting a first object to a second object. The method includes the steps of providing a first object that includes a main body portion and a neck extending upwardly from the main body portion, and providing a second object that includes a main body portion and a generally cylindrical connection member extending downwardly therefrom. The neck includes a first upper tab, a first lower tab and a first lug positioned between the first upper tab and first lower tab. The neck also includes a second upper tab, a second lower tab and a second lug positioned between the second upper tab and second lower tab. The connection member defines an axis and includes a bottom surface, an outer surface and an inner surface that defines a central opening, a first lower protrusion that includes first and second inclined surfaces extending inwardly from the inner surface, a first slot defined in the bottom surface and the inner surface, a first lower notch defined in the inner surface, and a first opening defined in the inner surface above the first lower protrusion. The first slot and the first lower notch are disposed on opposite sides of the first lower protrusion. The method further includes positioning the second object on the first object such that the neck is received in the central opening and the first lug is received in the first slot, and rotating the first object to a position where the first lower tab is positioned in the first lower notch and the first lug is positioned in the first opening. In a preferred embodiment, the first object is an electric toothbrush handle and the second object is an electric toothbrush head.

The invention, together with additional features and advantages thereof, may be best understood by reference to the following description.

DETAILED DESCRIPTION OF THE PREFERRED EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the-disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "upper," "lower," "side," "short," "long," "up," "down," and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, FIGS. 1-9 show an electric toothbrush 10 having a handle 12 and head 14 that are connected by a connection 16. It will be understood that the electrical components of the handle and the components for transmitting motion (e.g., rotational motion) to the toothbrush head and bristles are known. Therefore, a discussion of these components will be omitted. However, it should be understood that when the head 14 is docked with the handle 12, internal components on each come into mechanical communication, which allows the power supplied by the electrical components to rotate the bristles.

It should be further understood that the connection system described herein can be used for connecting any two objects and is not limited to an electric toothbrush.

Figure 1:
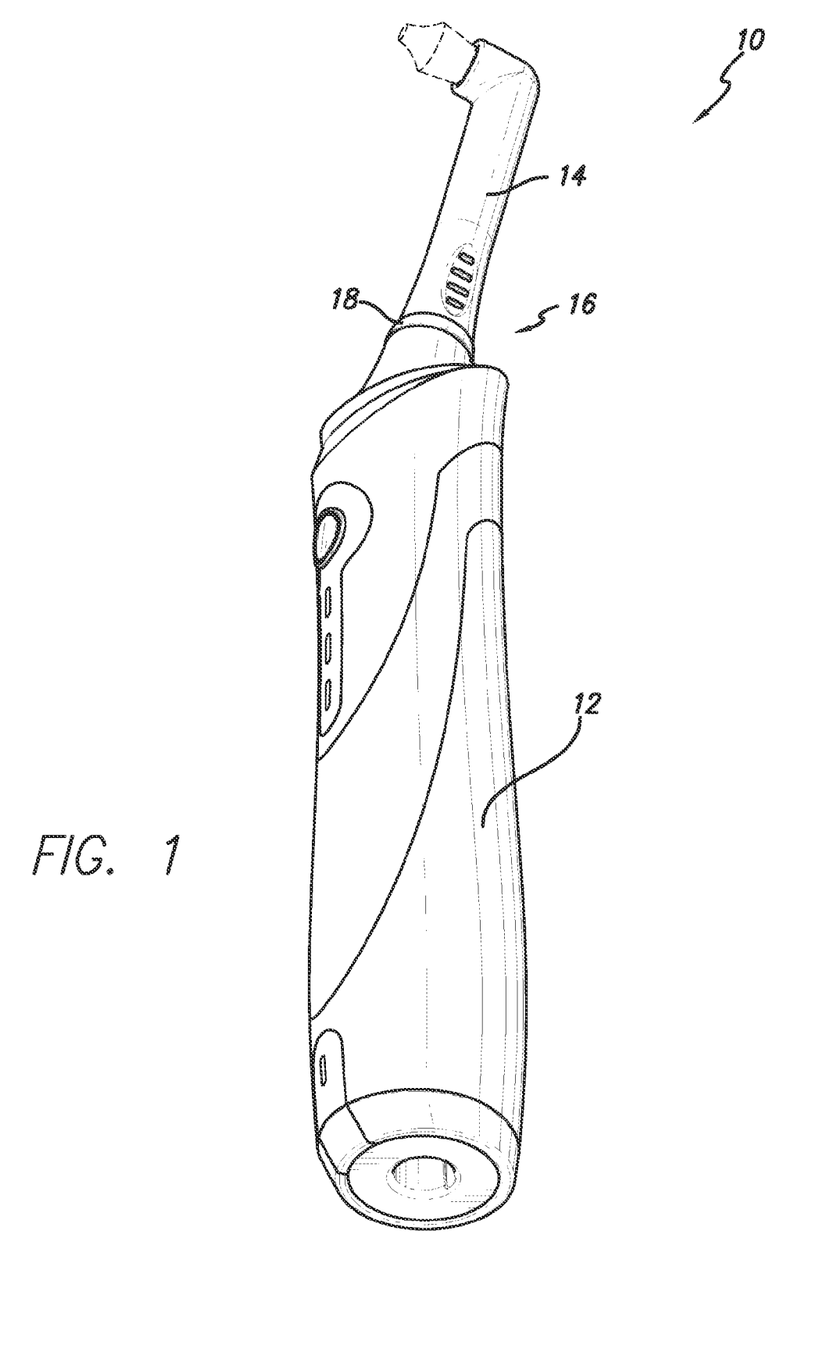
FIG. 1 is a perspective view of an electric toothbrush having a handle and head removably connected to one another in accordance with a first preferred embodiment of the present invention.
Figure 2:
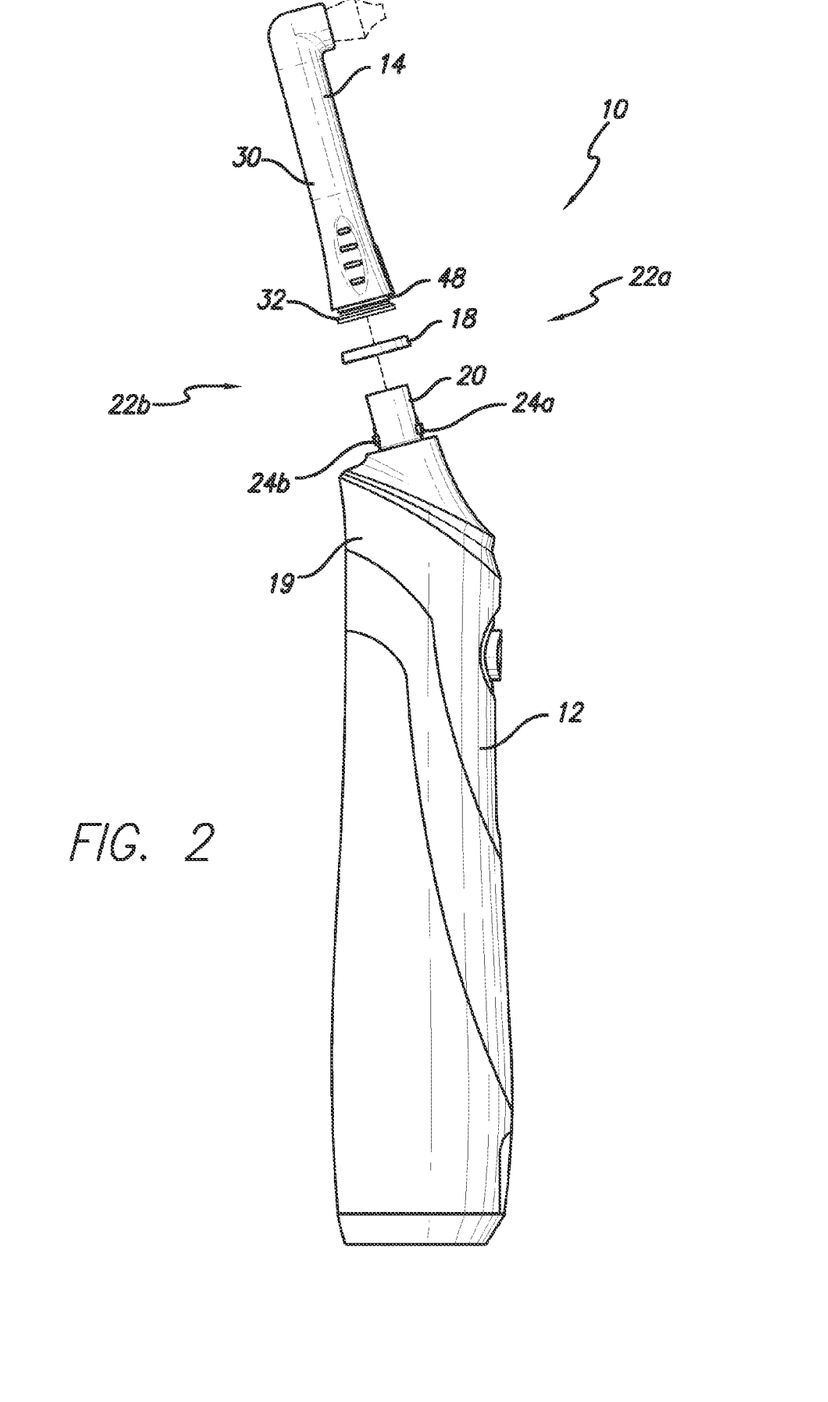
FIG. 2 is an exploded view of the electric toothbrush of FIG. 1.

As shown in FIG. 2, in a preferred embodiment, the toothbrush 10 includes the head 14, a ring 18, and the handle 12, which includes a main body portion 19 with a neck 20, for receiving or docking with the head 14. Generally, the head 14 docks with the neck 20 via a twisting or rotating motion and the interaction of the components on the head 14 and neck 20 retain the head 14 in place.

As shown in FIGS. 3-9, the connection 16 includes a front connection assembly 22a and a rear connection assembly 22b. It will be understood that the components associated with the front connection assembly 22a are all labeled with an "a" and the corresponding components associated with the rear connection assembly 22b are labeled with a "b." It will be further understood that, in a preferred embodiment, the only difference between the front and rear connection assemblies is the size of certain components (described below).

Figures 3, 3A, 3B:
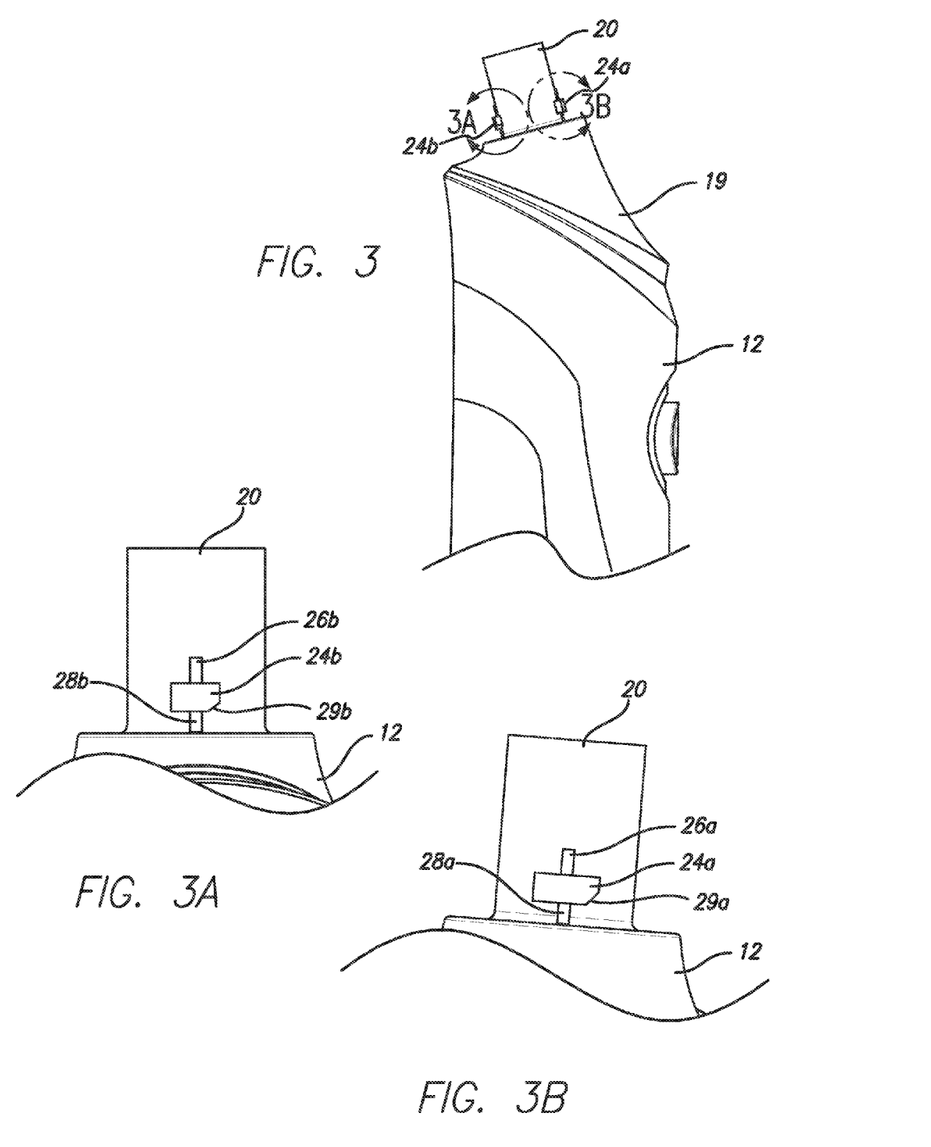
FIG. 3 is a side elevational view of the handle neck of the electric toothbrush of FIG. 1.
FIG. 3A is a detailed view of the back of the handle neck of the electric toothbrush of FIG. 1 showing the lug and tabs.
FIG. 3B is a detailed view of the front of the handle neck of the electric toothbrush of FIG. 1 showing the lug and tabs.

As shown in FIGS. 3-3B, the neck 20 includes front and rear lugs 24a and 24b, which each include upper tabs 26a and 26b and lower tabs 28a and 28b associated therewith. In a preferred embodiment, each of the lugs 24a and 24b include a bevel 29a and 29b.

Figure 4:
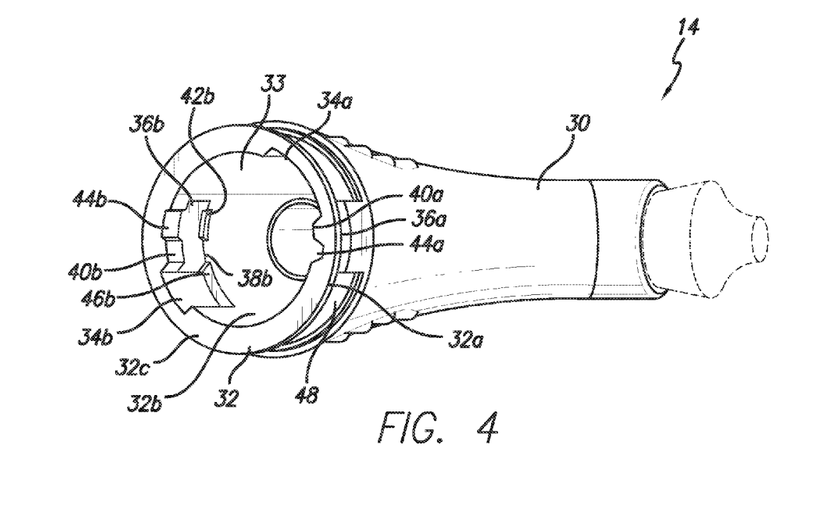
FIG. 4 is a perspective view of the inside of the bottom of the brush head of the electric toothbrush of FIG. 1.
Figure 5:
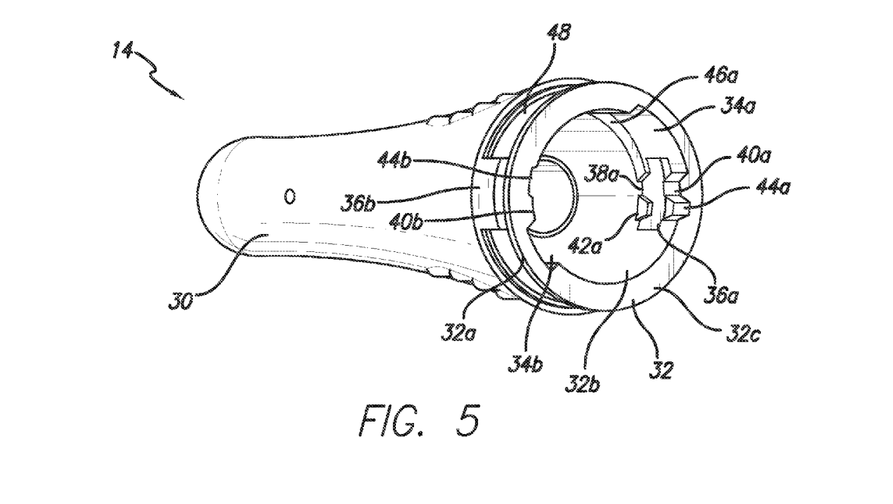
FIG. 5 is another perspective view of the inside of the bottom of the brush head of the electric toothbrush of FIG. 1.
Figure 6A:
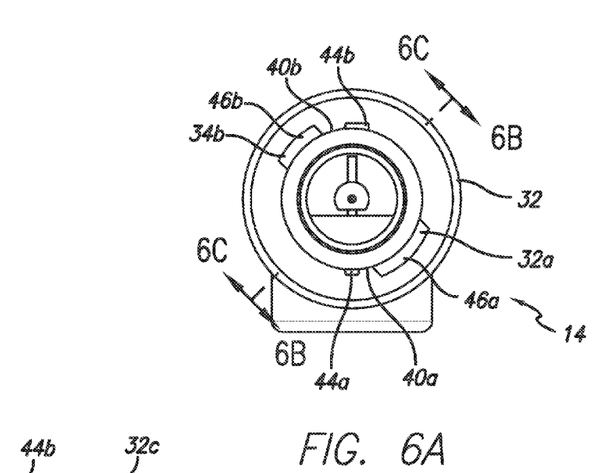
FIG. 6A is a bottom plan view of the brush head of the electric toothbrush of FIG. 1.
Figure 6B:
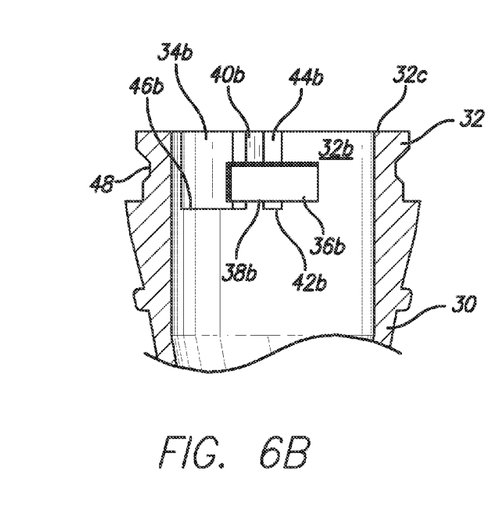
FIG. 6B is a cross-sectional view of a portion of the brush head taken along line 6B—6B of FIG. 6A.
Figure 6C:
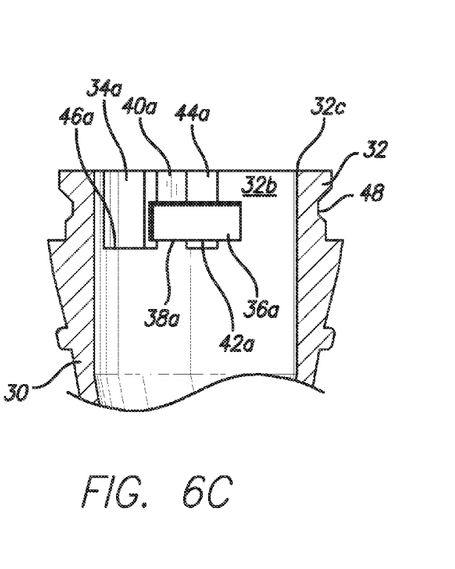
FIG. 6C is a cross-sectional view of a portion of the brush head taken along line 6C—6C of FIG. 6A.
Figure 7:
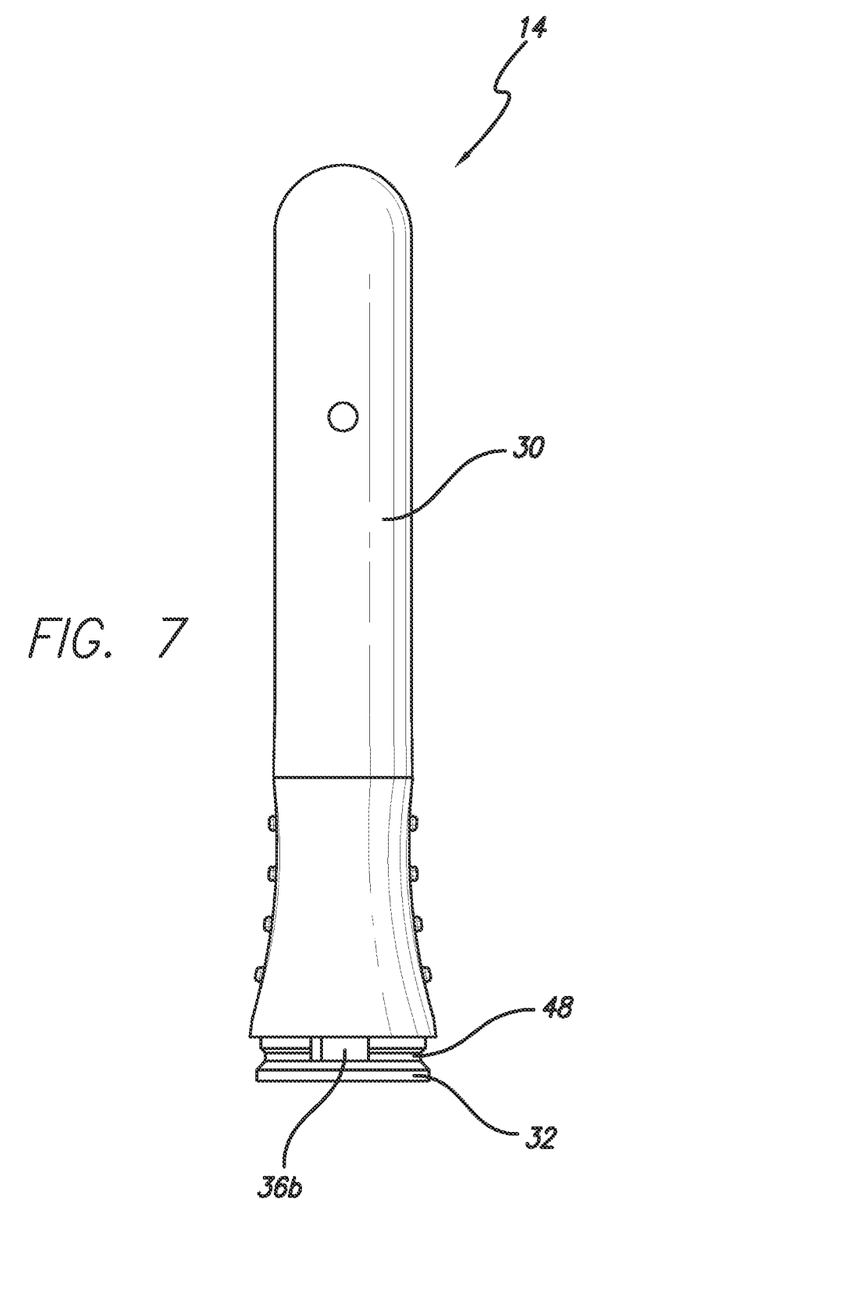
FIG. 7 is a rear elevational view of the brush head of the electric toothbrush of FIG. 1.
Figures 8, 9:
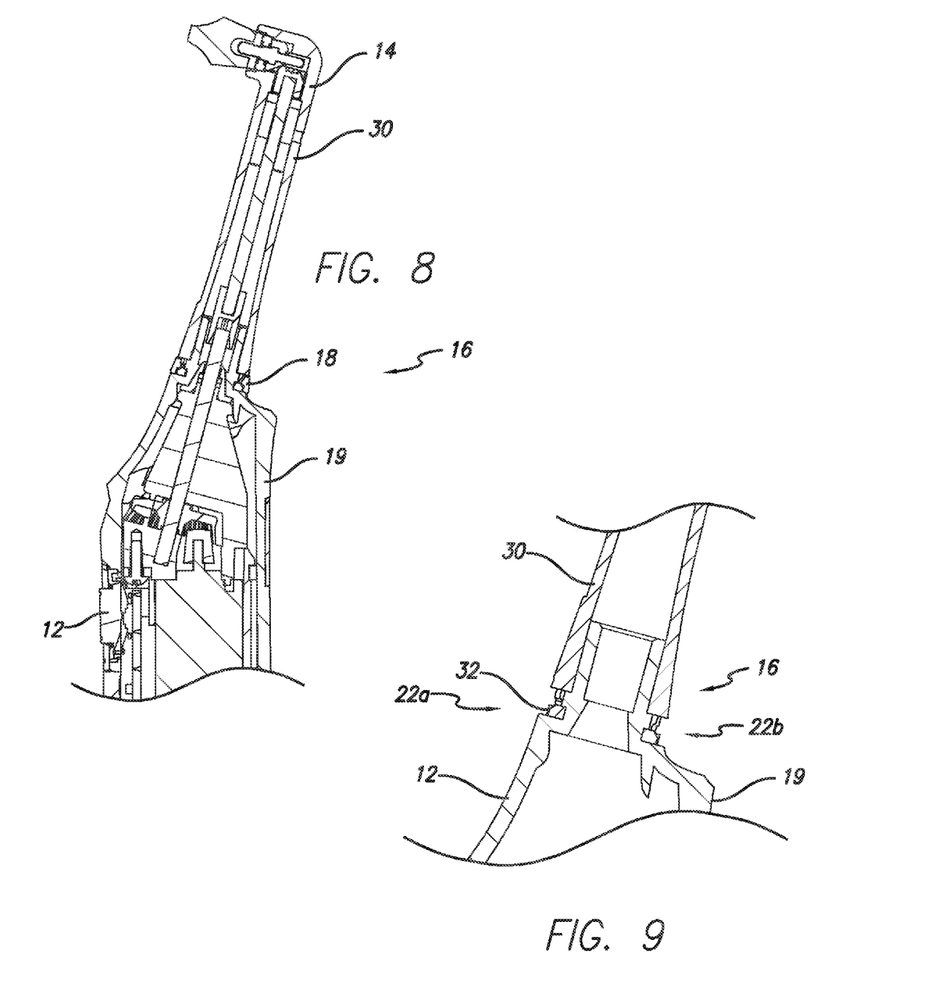
FIG. 8 is a cross-sectional view of the electric toothbrush of FIG. 1.
FIG. 9 is a cross-sectional view of the connection between the head and handle on the electric toothbrush of FIG. 1.

As is shown in FIGS. 4-6, head 14 includes a main body portion 30 with a connection member 32 extending downwardly therefrom. The connection member 32 includes an outer surface 32a, an inner surface 32b, a bottom surface 32b and a central opening 33, which is sized to receive neck 20. The connection member 32 also includes front and rear slots 34a and 34b which are sized to receive front and rear lugs 22a and 22b, respectively. The connection member 32 further includes front and rear openings 36a and 36b, front and rear upper protrusions 38a and 38b, front and rear lower protrusions 40a and 40b, front and rear upper notches 42a and 42b, front and rear lower notches 44a and 44b and front and rear abutment surfaces 46a and 46b.

It will be understood that the front and rear connection assemblies 22a and 22b connect in substantially the same way. Therefore, to simplify the description of the establishment of the connection, only the front connection assembly 22a will be described. This description also applies to the rear connection assembly 22b. In use, to establish the connection 16, the neck 20 is inserted into central opening such that slot 34a is aligned with lug 24a. Lug 24a is therefore received in slot 31a in a generally axial direction. At this point, the upper surface of lugs 24 should abut surface 46a (however, it does not have to).

Next, the head 14 is twisted or rotated in a clockwise direction and the inclined surfaces on upper and lower protrusions 38a and 40a contact upper and lower tabs 26a and 28a. In another embodiment, the rotation can be counterclockwise. As a result of the material that comprises the portion of the connection menìber 32 where the upper and lower protrusions 38a and 40a are disposed and the inclined surface, the upper and lower protrusions 38a and 40a flex outwardly to move passed the upper and lower tabs 26a and 28a, which results in the upper and lower tabs 26a and 28a seating/positioned in upper and lower notches 42a and 44a. Also, lug 24a is seated/positioned in opening 36a. It will be understood that bevel 29a is included to help position lug 24a properly during the twisting action. Bevel 29a contacts lower protrusion 40a and moves lug 24a upwardly if needed to properly seat lug 24a in opening 36a.

As shown in FIG. 6, slot 34a has a greater diameter or is deeper than upper and lower notches 42a and 44a. This helps hold the head 14 in place after being connected to the handle 12.

To undock the head 14 from neck 20 the head 14 is rotated counter-clockwise until lug 24a is positioned in slot 34a and then the head 14 is moved in a generally axial direction.

In a preferred embodiment, the connection member 32 includes a circumferential channel 48 defined in the outside surface 32a thereof for receiving the ring 18. Preferably, the circumferential channel 48 includes notches that receive protrusions on the inner diameter of the ring 18 and that prevent the ring 18 from rotating.

In a preferred embodiment, the front and rear lugs 24a and 24b and the corresponding front and rear slots 34a and 34b are sized such that head 14 cannot be installed backwards. As is shown in FIGS. 3A and 3B, front lug 24a has a greater length dimension than rear lug 24b. And, as shown in FIG. 6, front slot 34a has a greater width dimension than rear slot 34b. With this arrangement, front lug 24a will not fit in rear slot 34b, thus preventing accidentally placing the head 14 on backwards.

It will be understood that modifications can be made to the connection 16 and the components thereof. For example, the front connection assembly or the rear connection assembly can be omitted. Only one set of tabs, protrusions, and notches (either upper or lower) can be present and the other omitted. The bevels can be omitted. Openings 36a and 36b do not have to extend through the connection member, but can instead be troughs or the like.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further any specific numbers noted herein are only examples: alternative implementations may employ differing values or ranges.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

Accordingly, although exemplary enibodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A toothbrush head comprising:
    a main body portion; and
    a generally cylindrical connection member extending downwardly therefrom, wherein the connection member defines an axis, and wherein the connection member comprises:
    a bottom surface, an outer surface and an inner surface that defines a central opening,
    a first lower protrusion extending inwardly from the inner surface, wherein the first lower protrusion includes first and second inclined surfaces,
    a first slot defined in the bottom surface and the inner surface,
    a first lower notch defined in the inner surface, wherein the first slot and the first lower notch are disposed on opposite sides of the first lower protrusion, and
    a first opening extending through the connection member from the inner surface to the outer surface above the first lower protrusion,
    wherein a first lower tab is positioned in the first lower notch and the first lug is positioned in the first opening.

2. A toothbrush head comprising:
    a main body portion; and
    a generally cylindrical connection member extending downwardly therefrom, wherein the connection member defines a first axis, and wherein the connection member comprises:
    a bottom surface, an outer surface and an inner surface that defines a central opening,
    a first lower protrusion extending inwardly from the inner surface, wherein the first lower protrusion includes first and second inclined surfaces,
    a first slot defined in the bottom surface and the inner surface,
    a first lower notch defined in the inner surface, wherein the first slot and the first lower notch are disposed on opposite sides of the first lower protrusion,
    a first opening defined in the inner surface above the first lower protrusion,
    a first upper protrusion positioned above the first opening, and
    a first upper notch,
    wherein the first upper protrusion is substantially aligned with the first lower protrusion in a direction substantially parallel to the first axis, and wherein the first upper notch is substantially aligned with the first lower notch in a direction substantially parallel to the first axis.

3. The toothbrush head of claim 2 wherein the connection member further comprises a second lower protrusion extending inwardly from the inner surface, wherein the second lower protrusion includes first and second inclined surfaces,
    a second slot defined in the bottom surface and the inner surface,
    a second lower notch defined in the inner surface, wherein the second slot and the second lower notch are disposed on opposite sides of the second lower protrusion,
    a second opening defined in the inner surface above the second lower protrusion,
    a second upper protrusion positioned above the second opening, and a second upper notch, wherein the second upper protrusion is substantially aligned with the second lower protrusion in an axial direction and wherein the second upper notch is substantially aligned with the second lower notch in an axial direction.

4. The toothbrush head of claim 3 wherein the first opening and the second opening are positioned about 180° from one another.

5. A toothbrush head comprising:

a main body portion; and a generally cylindrical connection member extending downwardly therefrom, wherein the connection member defines an axis, and wherein the connection member comprises:

a bottom surface, an outer surface and an inner surface that defines a central opening, a first lower protrusion extending inwardly from the inner surface, wherein the first lower protrusion includes first and second inclined surfaces, a first slot defined in the bottom surface and the inner surface, a first lower notch defined in the inner surface, wherein the first slot and the first lower notch are disposed on opposite sides of the first lower protrusion, and a first opening defined in the inner surface above the first lower protrusion, a second lower protrusion extending inwardly from the inner surface, wherein the second lower protrusion includes first and second inclined surfaces, a second slot defined in the bottom surface and the inner surface, a second lower notch defined in the inner surface, wherein the second slot and the second lower notch are disposed on opposite sides of the second lower protrusion, and a second opening defined in the inner surface above the second lower protrusion.

6. The toothbrush head of claim 5 wherein the connection member further comprises a first upper protrusion positioned above the first opening, a first upper notch, wherein the first upper protrusion is substantially aligned with the first lower protrusion in an axial direction and wherein the first upper notch is substantially aligned with the first lower notch in an axial direction, a second upper protrusion positioned above the second opening, and a second upper notch, wherein the second upper protrusion is substantially aligned with the second lower protrusion in an axial direction and wherein the second upper notch is substantially aligned with the second lower notch in an axial direction.

7. The toothbrush head of claim 6 wherein the first opening and the second opening are positioned about 180° from one another.

* * * * *